US007175607B2

(12) United States Patent
Lim et al.

(10) Patent No.: US 7,175,607 B2
(45) Date of Patent: Feb. 13, 2007

(54) CATHETER BALLOON LINER WITH VARIABLE THICKNESS AND METHOD FOR MAKING SAME

(75) Inventors: Florencia Lim, Union City, CA (US); Edwin Wang, Tustin, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 435 days.

(21) Appl. No.: 10/382,965

(22) Filed: Mar. 6, 2003

(65) Prior Publication Data

US 2004/0176791 A1    Sep. 9, 2004

(51) Int. Cl.
A61M 29/00    (2006.01)

(52) U.S. Cl. .................... 604/103.06; 606/194

(58) Field of Classification Search ............. 604/96.01, 604/264, 101.01–103.14, 523–539, 284, 604/915–919; 606/191–194; 600/435, 115, 600/116
See application file for complete search history.

(56) References Cited

U.S. PATENT DOCUMENTS

| | | | |
|---|---|---|---|
| 4,638,805 A * | 1/1987 | Powell | 606/192 |
| 4,838,268 A * | 6/1989 | Keith et al. | 606/194 |
| 5,114,423 A * | 5/1992 | Kasprzyk et al. | 606/27 |
| 5,195,969 A | 3/1993 | Wang et al. | |
| 5,270,086 A | 12/1993 | Hamlin | |
| 5,334,146 A | 8/1994 | Ozasa | |
| 5,358,486 A * | 10/1994 | Saab | 604/103.13 |
| 5,458,568 A * | 10/1995 | Racchini et al. | 604/19 |
| 5,525,388 A | 6/1996 | Wand et al. | |
| 5,797,877 A | 8/1998 | Hamilton et al. | |
| 5,868,704 A | 2/1999 | Campbell et al. | |
| 5,879,369 A | 3/1999 | Ishida | |
| 6,004,289 A * | 12/1999 | Saab | 604/96.01 |
| 6,016,848 A | 1/2000 | Egres, Jr. | |
| 6,120,477 A | 9/2000 | Campbell et al. | |
| 6,203,735 B1 | 3/2001 | Edwin et al. | |
| 6,277,139 B1 | 8/2001 | Levinson et al. | |
| 6,375,637 B1 | 4/2002 | Campbell et al. | |
| 6,428,506 B1 * | 8/2002 | Simhambhatla et al. | 604/96.01 |

(Continued)

FOREIGN PATENT DOCUMENTS

WO    WO 95/05555    2/1995

(Continued)

*Primary Examiner*—Cris L. Rodriguez
(74) *Attorney, Agent, or Firm*—Fulwider Patton LLP

(57) ABSTRACT

A method of making a catheter balloon, and a balloon catheter formed thereby, in which a layer of a catheter balloon is formed by providing a tubular member to serve as a non porous liner for cooperation with a polymeric tube, and enlarging radially a central or working section of the tubular member such that a first end of the tubular member is smaller in the radial direction with respect to the working section. The tubular member may also have a thickness at the working section that is less than a thickness of the first and second end portions. The first end section of the tubular member is bonded to a catheter shaft having a first outer diameter to form at least a portion of a skirt section of the balloon, and the second end section is bonded to the catheter shaft having a second outer diameter to form a portion of a skirt section, where the skirt sections have an improved high rupture pressure.

10 Claims, 4 Drawing Sheets

U.S. PATENT DOCUMENTS

| | | |
|---|---|---|
| 6,436,135 B1 | 8/2002 | Goldfarb |
| 6,652,568 B1 * | 11/2003 | Becker et al. ............. 623/1.11 |
| 6,706,010 B1 * | 3/2004 | Miki et al. .................... 604/43 |
| 6,719,774 B1 * | 4/2004 | Wang ......................... 606/194 |
| 6,863,757 B1 * | 3/2005 | Gonzalez et al. ............. 156/86 |
| 6,902,571 B2 * | 6/2005 | Owens et al. ................ 606/194 |
| 6,939,321 B2 * | 9/2005 | Wang et al. ........... 604/103.08 |
| 2002/0082549 A1 * | 6/2002 | Duchamp ................ 604/96.01 |
| 2002/0146557 A1 * | 10/2002 | Claude et al. .............. 428/336 |
| 2003/0195510 A1 * | 10/2003 | Schaer ........................ 606/41 |
| 2004/0015183 A1 * | 1/2004 | Lim et al. ................... 606/194 |
| 2004/0068287 A1 * | 4/2004 | Lim et al. ................... 606/194 |
| 2004/0116957 A1 * | 6/2004 | Nishide et al. .............. 606/194 |
| 2005/0222584 A1 * | 10/2005 | Kilpatrick et al. .......... 606/108 |

FOREIGN PATENT DOCUMENTS

| | | |
|---|---|---|
| WO | WO 97/02791 | 1/1997 |

\* cited by examiner

CATHETER BALLOON LINER WITH VARIABLE THICKNESS AND METHOD FOR MAKING SAME

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians may implant an intravascular prosthesis, generally called a stent, inside the artery at the site of the lesion. Stents may also be used to repair vessels having an intimal flap or dissection or to generally strengthen a weakened section of a vessel or to maintain its patency. A tubular cover formed of synthetic or natural material may be present on an outer or inner surface of the stent. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed in place balloons, that are not folded prior to inflation, but which are instead expanded to the working diameter within the patient's body lumen from a generally cylindrical or tubular shape (i.e., essentially no wings) that conforms to the catheter shaft.

Catheter balloons formed of expanded polytetrafluoroethylene (ePTFE) expanded in place within the patient's body lumen provide an alternative to folded balloons. ePTFE is PTFE that has been expanded, and ePTFE typically has a microporous structure comprising nodes interconnected by fibrils.

Since compliant polymers such as ePTFE may be a porous material it is typically combined with a nonporous liner as part of the balloon's construction. The material used to form the liner may consist of a separate layer that neither fills the pores nor disturbs the node and fibril structure of the ePTFE or other polymeric layer, or it may at least partially fill the pores of the porous layer. The nonporous or low porosity liner is typically an elastomeric material that limits or prevents leakage of the inflation fluid through the microporous balloon layer when the balloon is inflated through pressurization via an inflation lumen. Another function of the nonporous liner is in deflating, i.e., restoring, the balloon to a low profile after inflation. The liner expands elastically during inflation of the balloon but has a shape memory such that, upon depressurization, the liner retracts the inflated polymeric layer back to a low profile configuration that promotes a safer withdrawal of the balloon catheter.

One difficulty has been providing an ePTFE balloon with sufficiently high rupture pressure. Some liner bonding techniques such as laser bonding the liner tubing to the outer surfaces of the catheter shaft results in wall thinning of the tubular liner in proximity with the bonding area. This reduction in wall thickness of the liner can be uneven and result in thin spots or weakened areas that place the integrity of the balloon at risk. Upon inflation of the balloon to elevated pressures of eight atmospheres or higher, these weaknesses due to the liner thinning at the bonding surfaces may lead to early rupture of the balloon. Stress concentrations are particularly elevated at the distal end of the balloon, where the inflection point of the tapered distal end portion and the bonded portion occurs.

SUMMARY OF THE INVENTION

This invention is directed to a method of making a catheter balloon liner, and a balloon catheter including the liner, in which the liner of a catheter balloon is formed by increasing the inner diameter of a first end section of a tubular member, so that the tubular member has a first end section with an inner diameter less than the inner diameter of a central section of the tube. The first end section may preferably have a diameter sized to coincide with the smaller outer diameter of the catheter shaft at the distal end of the balloon, and the liner is bonded thereto form at least a portion of a skirt section of the balloon, providing a skirt section with an improved high rupture pressure. By selecting a tubular member with dimensions for eliminating or minimizing the gap between the liner and the catheter shaft at the distal end of the balloon, the shortcomings resulting from mismatch bonding are ameliorated. Further, the liner can be expanded radially at the opposite end to also accommodate the larger outer diameter of the catheter shaft at the proximal end of the balloon, eliminating or minimizing the same shortcomings. Thus, the liner is modified from a constant diameter tubular member to a tubular member having varying radial dimensions in an undeformed state at various locations along the balloon's longitudinal location.

The method of making a catheter balloon liner of the invention generally comprises providing a tube having a central section and a first end section with an inner diameter, and increasing the inner diameter of the central section of the tube such that the diameter of the first end section is smaller in comparison therewith. In one embodiment, the central section of the tube is increased twenty three percent at the inner diameter in comparison with the inner diameter of the first end section. In a presently preferred embodiment, the inner diameter of the central section of the tube is increased by first extruding a tubular member of constant wall thickness and constant inner and outer diameter, and stretching the tubular member over a mandrel of greater outer diameter than the tubular member's inner diameter and heating the tubular member to a larger size at the middle portion. The outer surface of the mandrel may transition from a first outer diameter to a second larger outer diameter. The stretched tube is preferably heated on the mandrel in the stretched configuration to stabilize the tube in the stretched configuration, and the stretched tube may be further processed after heating and attached to a catheter shaft as part of the catheter balloon. The tubular liner may alternatively be formed by a single step extrusion process that yields a configuration wherein the first end has a substantially constant inner diameter and the middle portion has an inner diameter greater than the inner diameter of the first end in an undeformed state. Here, undeformed refers to the state of the liner before affixing the liner to the catheter shaft. This is to be distinguished from the assembled state where the attachment of the liner to the catheter shaft after bonding may result in a deformed state where the bonded ends are typically constricted in diameter compared with the unbonded working portion of the balloon due to the existence of the bonding. This is further distinguished from the pressurized state, in which the inner diameter of the balloon and its liner is enlarged at the working section during inflation and therefore greater than the end portions which are bonded to the catheter and do not expand.

The balloon of the present invention preferably has a wall thickness variation at the distal portion of the liner adjacent the bonded region compared with the thickness of the working section of the liner. Increasing the thickness of the liner at a first end portion, and preferably the distal end portion, in comparison with the central or working portion of the balloon liner, compensates for the thinning of the region adjacent the bonding regions due to the laser bonding techniques. The thicker wall fortifies the liner in the event of thin spots or high stress concentrations and improves the integrity of the balloon at elevated pressures. In a preferred embodiment the thickness of the balloon liner is greater at each end of the balloon adjacent the bonding region compared with the thickness of the liner at the working section of the balloon spaced from the tapered regions. In another embodiment, the liner is thicker at a first end, such as the distal end where the greatest stress concentrations statistically occur, and thinner at the working section and proximal section.

A balloon which embodies features of the invention can be used on a variety of suitable balloon catheters including coronary and peripheral dilatation catheters, stent delivery catheters, drug delivery catheters and the like. The balloon catheter of the invention generally comprises an elongated shaft having at least one lumen, and the balloon secured to a distal shaft section so that the balloon has an interior in fluid communication with the shaft lumen for delivery of inflation media to the balloon interior. The balloon typically has a proximal skirt/shaft section, a proximal tapered section, a working section, a distal tapered section, and a distal skirt/shaft section. The balloon has a liner that is bonded to the catheter shaft by a variety of suitable methods including fusion bonding and adhesive bonding.

The distal end section of the substantially non porous elastomeric tubular member preferably forms at least a portion of the distal tapered section of the balloon that fits over and adheres to the catheter shaft, and also preferably is sized radially to eliminate or minimize a gap between the inner diameter of the elastomeric liner and the outer diameter of the catheter shaft in an undeformed state prior to catheter assembly/inflation. The proximal end section may preferably be sized to eliminate or minimize the gap between the catheter shaft at its outer diameter and the inner diameter of the proximal end of the elastomeric liner. The elastomeric liner may change inner diameters between the distal end portion and the central working portion at a step, or may alternatively gradually taper from a first inner diameter and thickness at a first end to a second inner diameter and thickness at a middle portion, and possibly a third inner diameter and thickness at a second end.

In a preferred embodiment the distal end section of the elastomeric tubular liner mates with the catheter shaft without a gap therebetween in an undeformed state, and where the distal end section has a greater wall thickness compared to the central portion of the balloon. This configuration results in a liner with an improved rupture resistance after bonding the liner to the catheter. The high rupture pressure of the distal tapered section of the balloon adjacent the bonding region allows the balloon to be inflated at relatively higher inflation pressures. Moreover, the liner is formed of a smaller initial outer and inner diameters than other conventional liners because the liners are sized to accommodate the catheter shaft's inner tubular member in the undeformed state rather than the catheter's outer tubular member. This reduction can result in a lower profile liner at the distal end and ultimately a lower balloon profile at the distal end of the balloon.

In a presently preferred embodiment, the first layer is a porous polymeric material selected from the group consisting of expanded polytetrafluoroethylene (ePTFE), an ultra high molecular weight polyolefin including ultra high molecular weight polyethylene, porous polyolefins including polyethylene and polypropylene, and porous polyurethane. In one embodiment, the porous material has a node and fibril microstructure. ePTFE and ultra high molecular weight polyethylene (also referred to as "expanded ultra high molecular weight polyethylene") typically have a node and fibril microstructure, and are not melt extrudable. The node and fibril microstructure, when present, is produced in the porous material using conventional methods, and the layer of porous polymeric material preferably has the desired microstructure (e.g., porous and/or node and fibril) before being bonded to the catheter shaft. However, a variety of suitable polymeric materials can be used in the method of the invention including conventional catheter balloon materials which are melt extrudable.

In one presently preferred embodiment, the porous polymeric material forming the first layer cannot be formed into a balloon by conventional balloon blow molding, and is formed into a balloon by bonding a sheet of the porous polymeric material together to form a tubular member, and preferably provided with a nonporous second layer or liner to form an inflatable balloon. The porous polymeric layer is typically formed by wrapping a sheet of porous polymeric material on a mandrel and heating the wrapped sheet to fuse sections of the sheet together.

A preferred embodiment of the present invention provides a balloon catheter having a balloon outer layer of porous polymeric material and an inner layer of substantially non porous material secured to the catheter shaft by an improved bond achieved through selective dimensioning of the inner layer wall thickness and inner diameter to provide a catheter with improved rupture resistance adjacent the bond between the balloon tapered section and the catheter shaft. Moreover, the method provides a balloon having a lower profile and reduced thickness at the working portion of the balloon liner. These and other advantages of the invention will become more apparent from the following detailed description of the invention and the accompanying exemplary drawings.

DETAILED DESCRIPTION OF THE PREFERRED EMBODIMENTS

Figure 1:
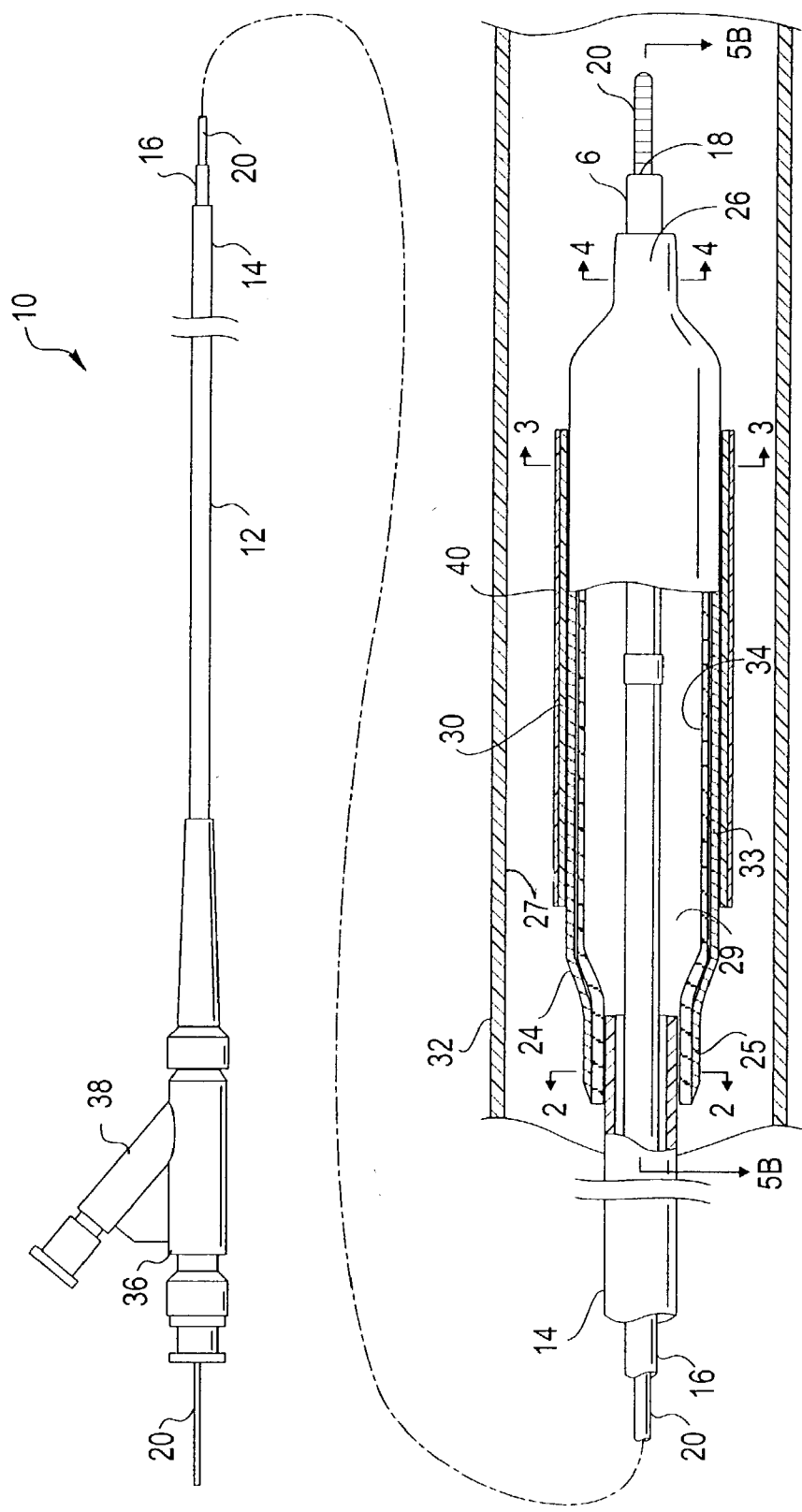
FIG. 1 is an elevational view, partially in section, of a stent delivery balloon catheter embodying features of the invention.
Figure 2:
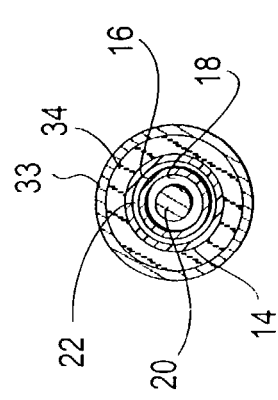
FIG. 2 is a transverse cross sectional view of the balloon catheter shown in FIG. 1, taken along line 2 2.

FIG. 1 illustrates an over the wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1, taken along line 2 2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 36 at the proximal end of catheter shaft 12 is configured to provide access to guidewire lumen 18, and to direct inflation fluid through arm 38 into inflation lumen 22. FIG. 1 illustrates the balloon 24 in an expanded configuration subsequent to inflation, with an expandable stent 30, with a stent cover 40 thereon, mounted on the balloon for delivery within a patient's body lumen 27. The distal end of the catheter may be advanced to a desired region of the body lumen 27 in a conventional manner, and balloon 24 inflated to expand covered stent 40, and the balloon deflated, leaving covered stent 40 implanted in the body lumen 27.

In the embodiment illustrated in FIG. 1, balloon 24 has a first layer 33 and a second layer 34. In a presently preferred embodiment, the balloon 24 first layer 33 comprises a microporous polymeric material, and preferably a microporous polymeric material having a node and fibril microstructure, such as for example ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that the first layer may comprise other materials, including ultrahigh molecular weight polyethylene. The second layer 34 is preferably formed of a thermoplastic elastomer such as Pursil AL 5 75A manufactured by Polymer Technology Group. In a preferred embodiment, layer 34 is an inner layer relative to layer 33, although in other embodiments it may be an outer layer. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer.

Figure 5A:
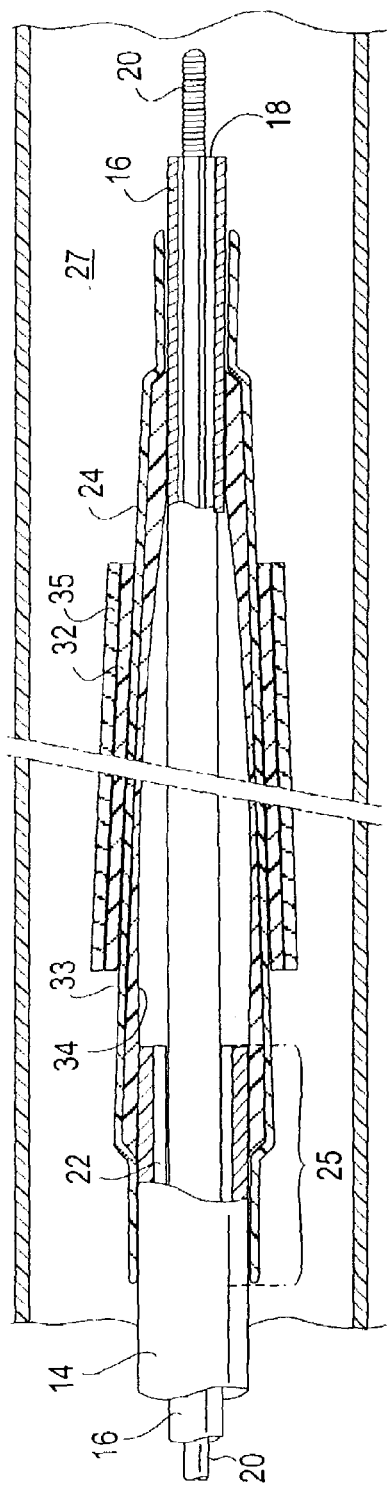
FIG. 5A is an enlarged longitudinal cross section of the balloon catheter of FIG. 1, taken along line 5B 5B in the deflated condition.
Figure 5B:
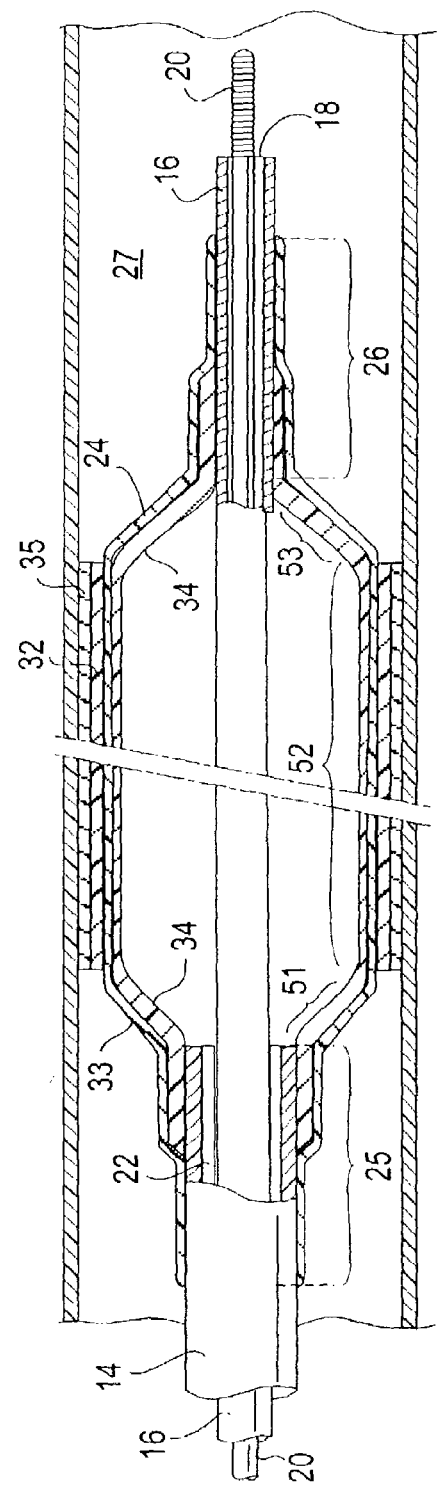
FIG. 5B is an enlarged longitudinal cross section of the balloon catheter of FIG. 1, taken along line 5B.

FIG. 5B is an enlarged, longitudinal cross section of the balloon catheter 10 of FIG. 1, taken along line 5B 5B. FIG. 5A illustrates the balloon catheter of FIG. 5B with the balloon in an uninflated configuration. The inflated balloon 24 has a central working section 52 with stent 32 mounted thereon, a proximal tapered section 51 between the working section 52 and the proximal skirt section 25, and a distal tapered section 53 between the distal skirt section 26 and the working section 52. The section of the first layer 33 extending along the working section of the balloon is hereafter referred to as the first layer working section, and the section of the second layer 34 extending along the working section of the balloon is hereafter referred to as the second layer working section or liner working section. Similarly, the first layer proximal and distal tapered sections refer to the sections of the first layer 33 extending along the proximal and distal tapered sections 51,53 of the balloon 24, and the first layer skirt sections refer to the sections of the first layer 33 extending along the balloon skirt sections 25, 26. In the same manner, the second layer proximal and distal tapered sections refer to the sections of the second layer 34 extending along the proximal and distal tapered sections 51,53 of the balloon 24, and the second layer skirt sections refer to the sections of the second layer 34 extending along the balloon skirt sections 25, 26. Although the balloon 24 is illustrated in FIG. 5B with a conventional inflated configuration having a central working length between two tapered inflatable sections, it should be understood that the inflated balloon may have a variety of suitable configurations including balloon configurations specially shaped for a particular anatomy such as a focal balloon configuration, a conical balloon configuration, and the like, as are conventionally known to one of skill in the art.

The first and second layers 33, 34 of balloon 24 each extend from the proximal skirt section 25 of the balloon to the distal skirt section 26 of the balloon. The first layer 33 can have a length which is the same as or shorter than the length of the second layer 34, but preferably will have end sections which extend beyond the end sections of the second layer 34 and onto the shaft. The skirt sections 25, 26 of the balloon typically comprise end sections of the second (inner) layer 34 having an inner surface bonded to the shaft, and sections of the first (outer) layer 33 having an inner surface bonded to the end sections of the second layer 34 which are bonded to the shaft. In the embodiment of FIGS. 5A and 5B, the skirt sections 25, 26 are also formed in part by end sections of the first layer 33 which extend beyond the end sections of the second layer 34 and which are bonded directly to the shaft without the second layer 34 or another member therebetween. The terminology "directly bonded" should be understood to include a variety of bonding methods including fusion and adhesive bonding.

To the extent not otherwise discussed herein, the various catheter components may be formed and joined by conventional materials and methods. For example, the outer tubular member can be formed by conventional techniques, such as by extruding and necking materials found useful in intravascular catheters such as polyethylene, polyvinyl chloride, polyesters, polyamides, polyimides, polyurethanes, and composite materials.

The length of the balloon catheter 10 is generally about 108 to about 200 centimeters, preferably about 137 to about 145 centimeters, and typically about 140 centimeters for PTCA. The outer tubular member 14 has an outer diameter (OD) of about 0.017 to about 0.036 inch (0.43 0.91 mm), and an inner diameter (ID) of about 0.012 to about 0.035 inch (0.30 0.89 mm). The inner tubular member 16 has an OD of about 0.017 to about 0.026 inch (0.43 0.66 mm), and an ID of about 0.015 to about 0.018 inch (0.38 0.46 mm) depending on the diameter of the guidewire to be used with the catheter. The balloon 24 has a length of about 8 mm to about 80 mm, typically about 8 mm to about 38 mm, and an inflated working diameter of about 1.5 mm to about 20 mm, typically about 2 mm to about 10 mm.

Figure 4:
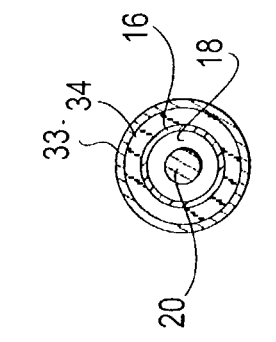
FIG. 4 is a transverse cross sectional view of the balloon catheter shown in FIG. 1, taken along line 4 4.
Figure 3:
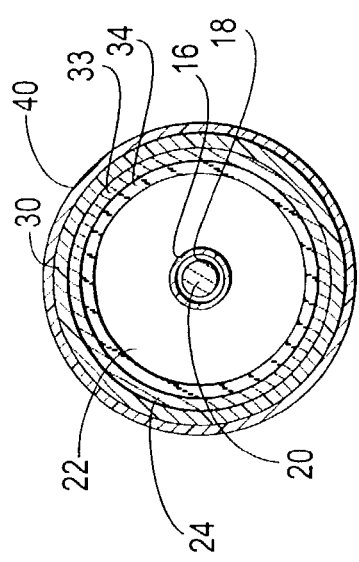
FIG. 3 is a transverse cross sectional view of the balloon catheter shown in FIG. 1, taken along line 3 3.

FIGS. 2–4 illustrate cross sectional views of the balloon assembly at the proximal skirt section 25, at the working length 52, and the distal skirt section 26, respectively, of the balloon 24. Each figure illustrates from the center outward, the guidewire 20, guidewire lumen 18, and inner tubular member 16. FIG. 2 further illustrates inflation lumen 22, outer tubular member 14, second (inner) layer 34, and first (outer) layer 33. In FIG. 3, progressing radially outward from the inner tubular member 16 is the balloon interior 29, second (inner) layer 34, first (outer) layer 33, stent 30, and stent cover 40. In FIG. 4 progressing radially outward from the inner tubular member 16 is the second (inner) member 34 and the first (outer) member 33. Of significance is the thickness of the second (inner) layer 34 at the distal skirt section 26 and its relative increase over the thickness of the second (inner) layer 34 at the working section 52 as shown in FIGS. 4 and 3, respectively. The thickness of the second layer 34 at the distal tapered portion 53 is substantially the same as the thickness of the distal skirt section and represents an increased thickness in relation to the working length of the second layer. This can be seen in FIGS 5A and 5B, where the thickness of the second layer at the tapered portions 51, 53 are greater than the thickness of the working portion 52. Because the tapered portions 51,53, and in particular distal tapered portion 53 is susceptible to thinning and weak spots that may promote early rupture at elevated pressures, the thickness increase helps to safeguard against the premature rupture by providing a stronger structure at the point of failure.

Figure 6:
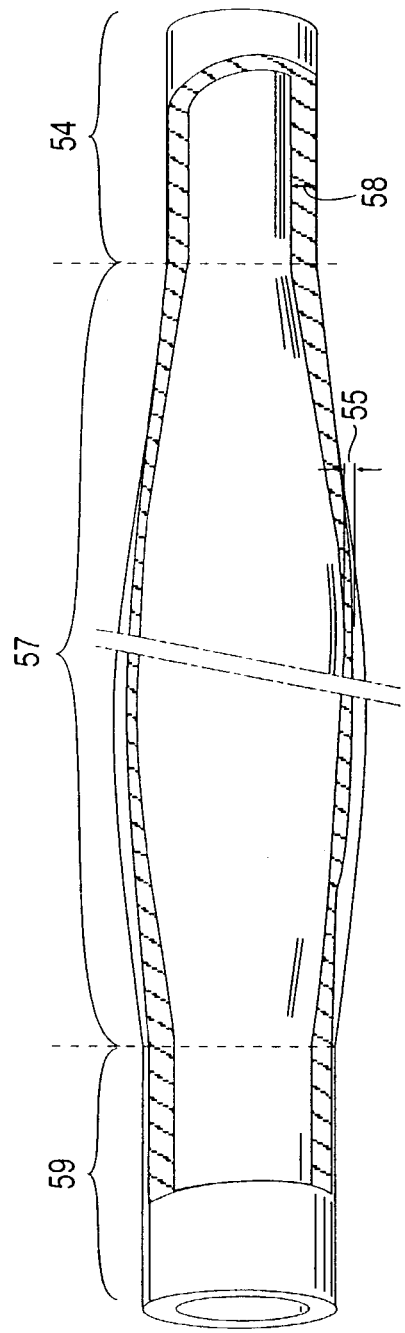
FIG. 6 illustrates a first preferred embodiment of a tubular liner of the present invention in an undeformed state prior to attachment to a catheter shaft

FIG. 6 illustrates the second layer 34 in an undeformed state prior to bonding with the catheter. In its undeformed state, the tubular liner comprises a first section 54 of substantially constant inner diameter and outer diameter with a first thickness 58. The first section comprises both the distal skirt portion 26 and the distal tapered portion 53. The second layer 34 increases in inner diameter away from first section 54 at a second section 57, by a step increase or preferably in a gradually tapered configuration such as that shown in FIG. 6. The transition from the tapered portion 53 to the working length and the resulting change in thickness is reflected in the thickness 55 of the second section 57 compared with the thickness 58 of the first section. In a preferred embodiment, the thickness at the proximal end 59 of the second layer 34 is also greater than the thickness 55 of the working length 57. The inner diameter of the second layer 34 at the proximal end portion may level out to a constant diameter section along the proximal skirt portion of the liner.

A dimensional example is illustrative. For a catheter assembly utilizing a outer member 14 having an inner diameter of 0.027 inches and an outer diameter of 0.031 inches at the balloon's proximal end, and a inner tubular member 16 having an inner diameter of 0.016 inches and an outer diameter of 0.022 inches at the balloon's distal end, the liner shown in FIG. 6 may have a distal section 54 having an inner diameter in the range of 0.019 to 0.026, and more preferably in the range of 0.021 to 0.023, and even more preferably 0.022 inches to match the outer diameter of the inner tubular member 16. The outer diameter of the liner at the distal section is preferably in the range of 0.026 to 0.031 inches, and more preferably 0.027 to 0.030 inches, and even more preferably 0.028 inches. The thickness of the liner at the distal section is preferably 0.004 to 0.008 inches, and more preferably 0.005 to 0.007 inches, and even more preferably 0.006 inches in the skirt and taper portions of the liner. The inner diameter of the liner in the working section is preferably in the range of 0.026 to 0.032 inches, and more preferably between 0.027 to 0.030 inches, and even more preferably between 0.028 to 0.030 inches. The outer diameter expands also to a range of 0.029 inches to 0.035 inches, and more preferably between 0.030 to 0.034 inches, and even more preferably between 0.031 to 0.033 inches. These ranges are illustrative only. The greater expansion of the inner diameter of the working section with respect to the outer diameter corresponds with a reduction in the thickness of the liner of approximately one half while the diameter of the liner expands compared with the distal end portion. The thickness of the liner may increase back to the thickness of the distal section, or slightly less such as 0.005 inches to account for stress concentrations at the proximal tapered portion. Here, the slight reduction in thickness in comparison to the distal section accounts for the slightly reduced stress concentrations at the proximal tapered portions because the juncture between the balloon tapered portion and the balloon skirt section at the proximal end portion is slightly less oblique than at the distal end.

In contrast with previous liner configurations with a constant inner diameter sized to accommodate the outer tubular member 14 in an undeformed state, which left an appreciable mismatch at the distal end where the liner was bonded to the smaller inner member 16, the present liner configuration preferably eliminates or minimizes the mismatch between the liner 34/inner tubular member 16 juncture while not introducing a mismatch of the liner 34/outer tubular member 14 juncture. The fitting of the liner at the respective ends of the balloon reduces stress after the bonding stage and increases the integrity of the balloon. Moreover, the increased thickness of the liner at the tapered regions of the inflated balloon fortify the balloon liner at a vulnerable location and increases the capability of the balloon to higher inflation pressures with a lower risk of rupture.

Figure 7:
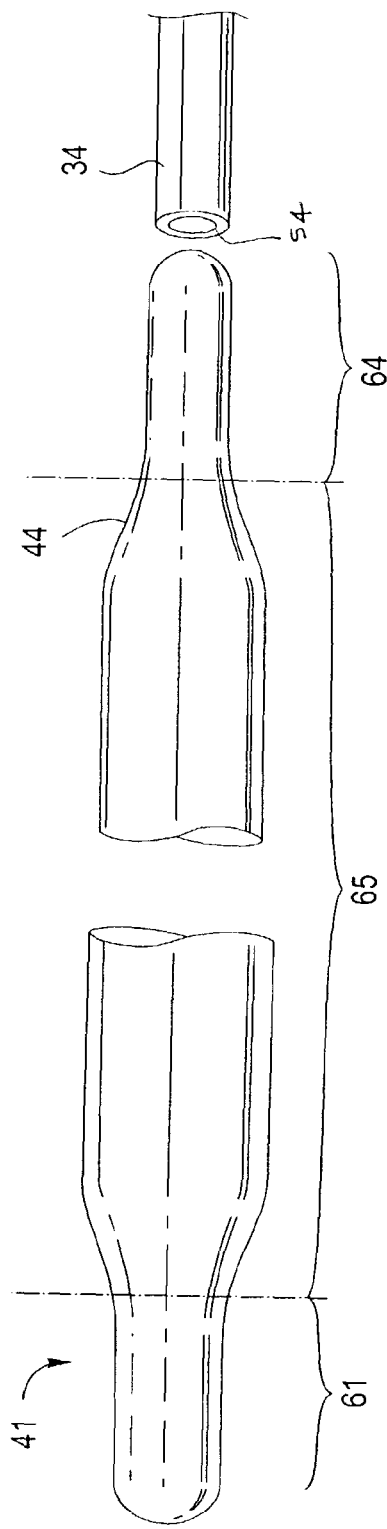
FIG. 7 illustrates a liner and mandrel combination for forming the embodiment of FIG. 6.
Figure 8:
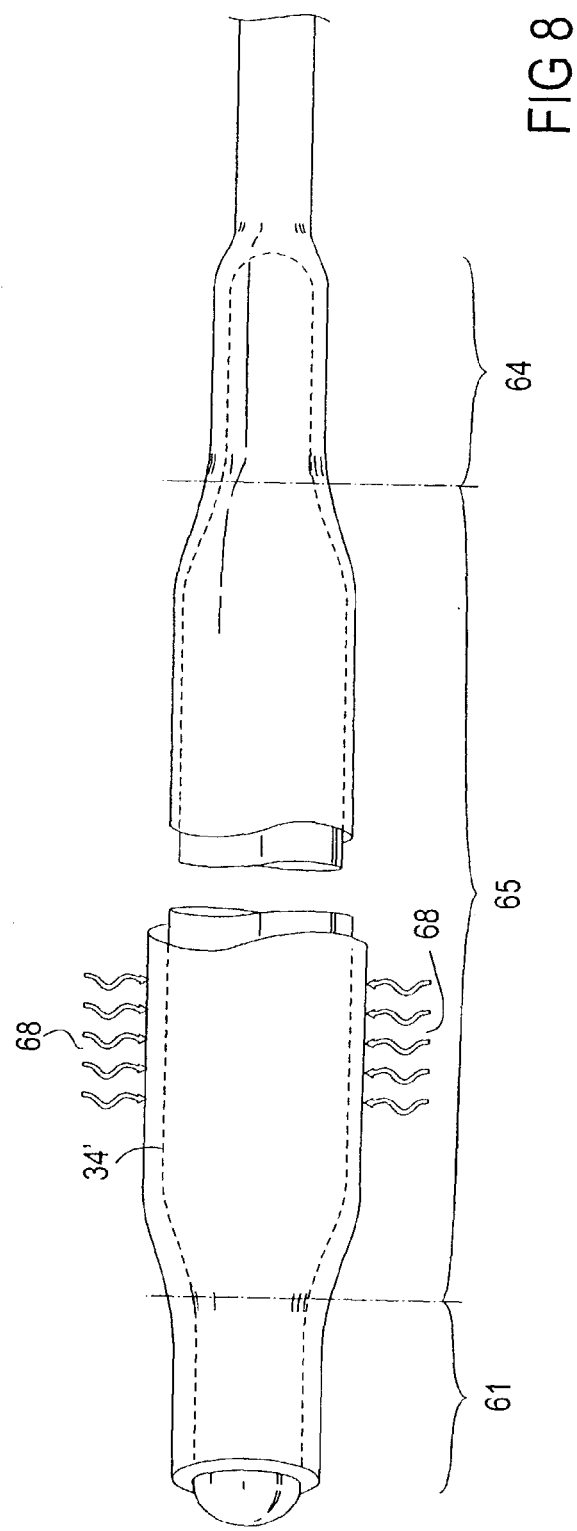
FIG. 8 illustrates the porous polymeric tube of FIG. 6, positioned on the mandrel of FIG. 7.

FIGS. 7 and 8 illustrate an assembly of an elastomeric liner 34 on a mandrel 41, during formation of a layer of a catheter balloon in a method which embodies features of the invention. The elastomeric material of the tube 34 is a thermoplastic such as Pursil AL 5 75A in the embodiment in which the tube forms second (inner) layer 34 of the balloon 24 of FIG. 1. The mandrel 41 has a first section 64 with a first outer diameter corresponding to the distal end of the liner, and a second section 65 with an outer diameter greater than the outer diameter of section 64. The mandrel can have a variety of suitable configurations consistent with the teachings of the present disclosure. For example, although the mandrel second section 65 may have a gradually increasing diameter, in an alternative embodiment, the second section 65 may have a constant inner and outer diameter after a stepped increase in the inner and outer diameters, or a tapered portion followed by a constant diameter portion.

FIG. 7 illustrates the liner 34 and its relative size adjacent the bigger mandrel 41 before the liner is longitudinally stretched onto the mandrel. The mandrel is divided into at least a proximal end section 61, central section 65, a tapered region 44 and a distal section 64. The distal section 64 of mandrel 41 has an outer diameter which is preferably only slightly larger than the inner diameter of the distal section 54 of the elastomeric liner 34. The outer diameter of the mandrel distal section 64 is approximately 0.027 inches.

As shown in FIG. 8, the mandrel 41 is inserted into the liner 34 to expand the liner. The liner 34 may be subject to elevated temperatures during the stretching process, or alternatively the stretching may take place at ambient (i.e., room) temperature. FIG. 8 illustrates the liner 34 of FIG. 7 after being radially expanded by the surface of the mandrel 41 to form longitudinally stretched tube 34'. The stretched tube 34' has an increased diameter at central section 65 larger than the diameter at distal section 64.

Also shown in FIG. 8 are arrows 68 representing a processing step to reduce the thickness of the liner 34 within section 65. The arrows 68 may represent selective elevated heating to reduce the thickness of the liner at the working section of the balloon, or the arrows may represent another process to thin the liner. Alternatively, the liner thickness may be reduced during the formation of the liner such as with a hypotube that blows air during the curing step to reduce the thickness of the liner at the working section, or the liner may be extruded in a single step to include the thickness variations.

Balloon 24 of catheter 10, formed according to a method embodying features of the invention, preferably has a distal skirt section 26 with a rupture pressure of about 14 atm (210 psi) to about 28 atm (410 psi) depending on the desired working pressure of the balloon 24. In the embodiment in which balloon 24 is a relatively high pressure balloon (i.e., rated to about 18 atm or above), the distal skirt section 26 preferably has a rupture pressure of not less than about 22 atm (320 psi). Similarly, a proximal skirt section formed according to the method of the invention with a first layer reduced diameter end section would have rupture pressure similar to the distal skirt section, and generally of not less than 20 atm.

While the present invention has been described herein in terms of certain preferred embodiments, those skilled in the art will recognize that modifications and improvements may be made without departing from the scope of the invention. For example, although the embodiment illustrated in FIG. 1 is an over the wire stent delivery catheter, balloons of this invention may also be used with other types of intravascular catheters, such as rapid exchange balloon catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. Additionally, although not illustrated, a soft distal tip member may be provided at the distal end of the catheter, and bonded to the balloon distal skirt section 26, as is conventionally known. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter comprising:
   a) a catheter shaft having a proximal end, a distal end, and an inflation lumen extending therein; and
   b) a balloon disposed on a distal shaft section, the balloon having a tubular, essentially wingless noninflated configuration inflatable to an inflated configuration, an inflatable working section, a proximal skirt section, and a distal skirt section, the proximal and distal skirt sections of the balloon being sealingly secured to the shaft so that an interior of the balloon is in fluid communication with the inflation lumen, the balloon comprising a porous polymeric first layer, and a second layer secured at least in part to the first layer, the first and second layers each extending from the proximal skirt section to the distal skirt section, the second layer having a varying wall thickness along a length thereof such that the wall thickness of the second layer along the working section is less than along the proximal and distal skirt sections in the noninflated configuration, and the first layer having a wall thickness that does not vary from the proximal skirt section to the working section in the noninflated configuration.

2. The balloon catheter of claim 1 wherein the porous polymeric first layer is comprised of a material from a group comprising expanded polytetrafluoroethylene (ePTFE), ultra high molecular weight polyethylene, porous polyolefins, and porous polyurethane.

3. The balloon catheter of claim 1 wherein the second layer is an inner layer relative to the first layer.

4. The balloon catheter of claim 3 wherein the first layer is comprised of expanded polytetrafluoroethylene.

5. The balloon catheter of claim 1 wherein the distal end section of the second layer has a first wall thickness greater than a third wall thickness of the second layer at the proximal end section in the noninflated configuration.

6. The balloon catheter of claim 5 wherein the proximal end section of the second layer has a third wall thickness greater than a second wall thickness at the working section.

7. A balloon catheter comprising:
   a) a catheter shaft having a proximal end and a distal end;
   b) a balloon disposed on the catheter shaft at the distal end, the balloon having a tubular, essentially wingless noninflated configuration inflatable to an inflated configuration, an inflatable working section, a proximal skirt section, and a distal skirt section, the proximal and distal skirt sections of the balloon being sealingly secured to the shaft so that an interior of the balloon is in fluid communication with the inflation lumen, and further comprising a tubular outer layer comprising expanded polytetrafluoroethylene and a non-porous inner liner layer, the liner layer having a first thickness at a first end that is greater than a second thickness at the working section in an undeformed state such that the wall thickness of the liner layer along the working section is less than along the proximal and distal skirt sections in the noninflated configuration, and the expanded polytetrafluoroethylene outer layer has a wall thickness along the working section that is not less than along the proximal skirt section in the noninflated configuration.

8. The balloon catheter of claim 7 wherein the non-porous liner includes a third thickness at a second end and the third thickness is greater than the second thickness at the working length.

9. The balloon catheter of claim 8 wherein the first end of the non-porous liner is at the distal end of the balloon and the second end of the non-porous liner is at the proximal end of the balloon, and the first thickness is greater than the third thickness.

10. The balloon catheter of claim 8 wherein the first end of the non-porous liner is at the distal end of the balloon and the second end of the non-porous liner is at the proximal end of the balloon, and the first thickness is equal to the third thickness.

* * * * *